United States Patent [19]
Rueb et al.

[11] Patent Number: 5,296,451
[45] Date of Patent: Mar. 22, 1994

[54] CINNAMIC ESTERS

[75] Inventors: Lothar Rueb, Speyer; Karl Eicken, Wachenheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 920,816

[22] Filed: Jul. 27, 1992

Related U.S. Application Data

[63] Continuation of Ser. No. 557,063, Jul. 25, 1990, abandoned.

[30] Foreign Application Priority Data

Jul. 26, 1990 [DE] Fed. Rep. of Germany ....... 3924719

[51] Int. Cl.$^5$ .................. C07D 513/04; A01N 43/90
[52] U.S. Cl. .................... 504/236; 544/235
[58] Field of Search .................. 544/235; 504/235

[56] References Cited

U.S. PATENT DOCUMENTS 5,035,740  7/1991  Poss ..................... 504/236

FOREIGN PATENT DOCUMENTS 61-27962  2/1986  Japan .

Primary Examiner—Robert Gerstl
Attorney, Agent, or Firm—Keil & Weinkauf

[57] ABSTRACT

Cinnamic esters of the formula I

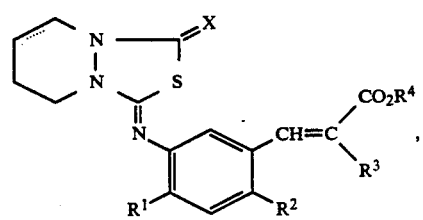

where the dotted bond is a single or double bond, $R^1$ is hydrogen or fluorine, $R^2$ is halogen, $R^3$ is hydrogen, halogen or $C_1$–$C_4$-alkyl, $R^4$ is hydrogen, substituted or unsubstituted $C_1$–$C_6$-alkyl, or is $C_3$–$C_6$-alkenyl, $C_3$–$C_6$-alkynyl or benzyl, and X is oxygen or sulfur, processes for their manufacture, and agents containing them.

6 Claims, No Drawings

CINNAMIC ESTERS

This application is a continuation of application Ser. No. 07/557,063, filed on Jul. 25, 1990, now abandoned.

The present invention relates to novel cinnamic esters of the formula I,

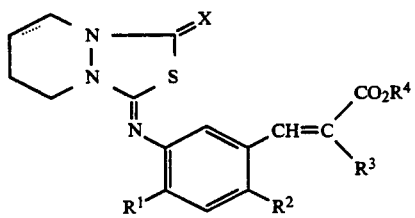

where the dotted bond is a single or double bond, $R^1$ is hydrogen or fluorine, $R^2$ is halogen, $R^3$ is hydrogen, halogen, or $C_1$-$C_4$-alkyl, $R^4$ is hydrogen or $C_1$-$C_6$-alkyl which may be substituted by one or two $C_1$-$C_4$-alkoxy groups, or is $C_3$-$C_6$-alkenyl, $C_3$-$C_6$-alkynyl or benzyl, and X is oxygen or sulfur.

The present invention furthermore relates to processes for the preparation of these compounds and herbicides containing the cinnamic esters I.

JP-A 2,7962/1986 discloses 5-(N-tetrahydrophthalimido)cinnamic acid derivatives as herbicides, which however are unsatisfactory with regard to the required application rates.

It is an object of the present invention to provide particularly active herbicidal compounds.

We have found that this object is achieved by the cinnamic esters defined at the outset.

The compounds I are obtained, for example, by converting an aminocinnamic acid derivative of the general formula II in a conventional manner (Houben-Weyl, Vol. IX, page 867 et seq. (1955)) in an inert organic solvent with thiophosgene into the corresponding isothiocyanate III, then subjecting III to an addition reaction with the tetrahydro- or perhydrodiazine derivative IV in an aprotic polar solvent and subjecting the resulting thiourea V to a cyclization reaction with a phosgenating agent or thiophosgenating agent (Phos.) to give I.

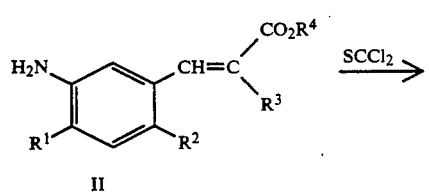

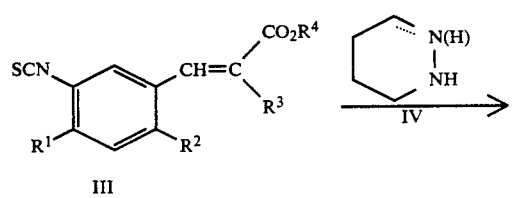

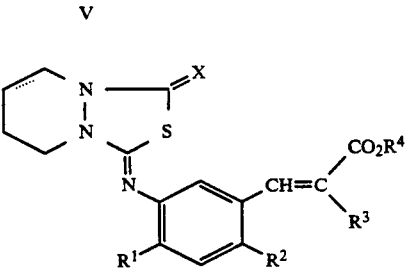

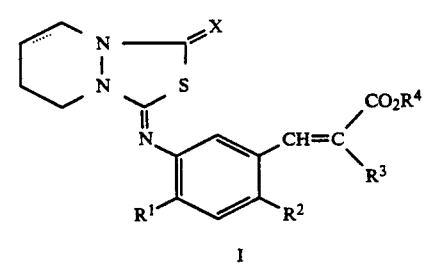

The reaction of the aminocinnamic acid derivative II with thiophosgene is carried out as a rule at from −50° to 100° C., preferably from 0° to 50° C.

This reaction can be carried out both in a two-phase solvent system, such as methylene chloride/water and in the presence of a base in an aprotic polar organic solvent. In the last-mentioned case, the reaction is preferably carried out in toluene in the presence of an organic base, preferably a tertiary amine, such as triethylamine.

The aminocinnamic acid derivatives required for the reaction are obtained, for example, by reduction of the corresponding nitrocinnamic acid derivatives by known methods (DE-A 3,724,399 and DE-A 3,603,789). The reaction of the isothiocyanates III with the piperazines IV is preferably carried out in aprotic polar solvents, preferably ethers, in particular tetrahydrofuran, at from −50° to 100° C., preferably from 0° to 50° C. The subsequent cyclization of the thiourea V with a phosgenating agent or thiophosgenating agent is effected as a rule at from 0° to 100° C., preferably from 20° to 70° C., in an aprotic polar solvent in the presence of a base, particularly suitable phosgenating agents and thiophosgenating agents being phosgene, thiophosgene and trichloromethyl chloroformate.

Preferably used solvents are ethers, halohydrocarbons and hydrocarbons, in particular halohydrocarbons such as methylene chloride. Suitable bases are tertiary amines, in particular pyridine.

However, the compounds of the formula I are also obtained if, in accordance with the conditions described above, an aniline derivative of the formula VI is first converted with thiophosgene into the corresponding isothiocyanate IIIa, IIIa is subjected to an addition reaction with a piperazine IV, the resulting thiourea derivative Va is subjected to a cyclization reaction with a phosgenating agent, with acidic cleavage of the acetal group to the aldehyde function, to give the aldehyde VII, and VII is reacted with a phosphorylide of the formula VIII.

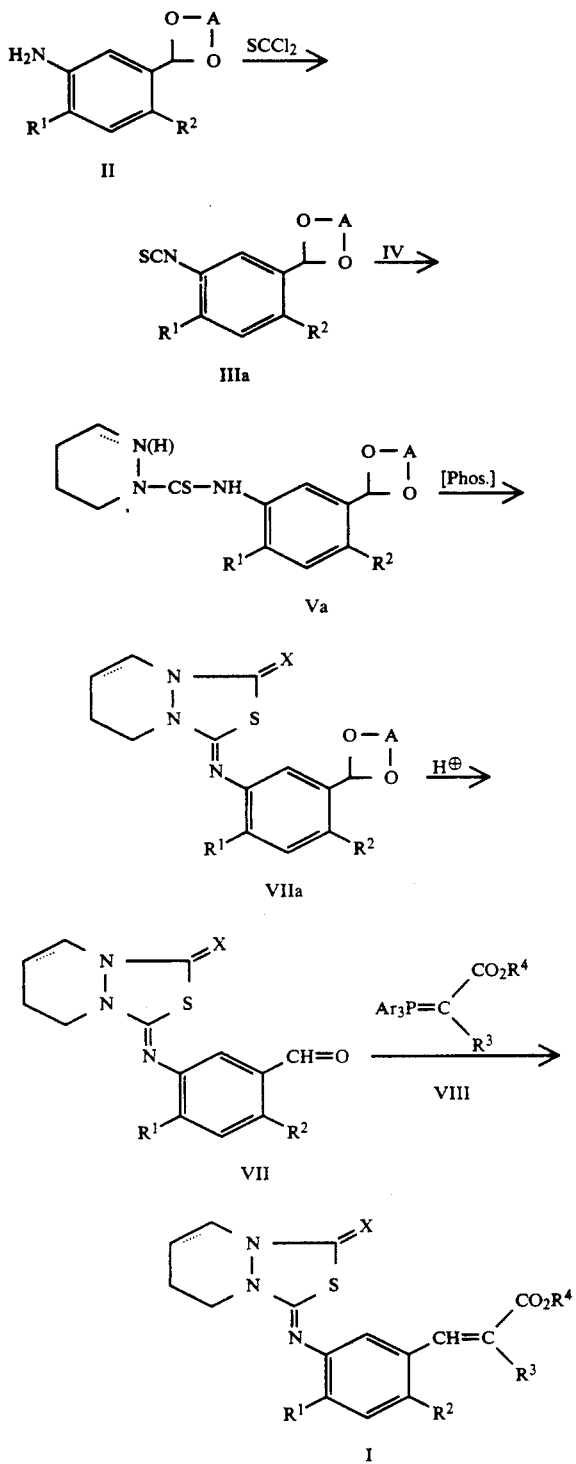

In the formulae VI, IIa, Va and VIIa, A is an ethylene or propylene unit which may carry one to three alkyl groups, such as methyl, ethyl, propyl or 1-methylethyl, preferably methyl.

The conversions of VII to IIIa, of IIIa to Va and of Va to VIIa take place under the conditions described above, similarly to the first synthesis variant. The acetal group in compound VIIa is converted into the aldehyde function under acidic conditions, for example in the presence of mineral acids, such as hydrochloric acid and sulfuric acid or organic acids such as p-toluenesulfonic acid.

The reaction of the resulting aldehyde VII with the phosphorylide VIII is carried out in a conventional manner (e.g. DE-A 3,904,082), in an inert organic solvent, such as toluene, teterahydrofuran, dimethylformamide, dimethyl sulfoxide or methanol.

In formula VIII Ar is unsubstituted or substituted aryl, phenyl generally being preferred.

The phosphorylides VIII required for the reaction are obtained by methods similar to conventional ones (e.g. Chem. Ber. 95 (1962), 3003).

In view of the intended use of compounds I as herbicides, preferred substituents are the following radicals:

$R^1$ is hydrogen or fluorine;

$R^2$ is halogen, such as fluorine, chlorine or bromine, in particular chlorine;

$R^3$ is hydrogen; halogen as stated under $R^2$, in particular chlorine or bromine; alkyl, such as methyl, ethyl, propyl, 1-methylethyl, butyl, 1-methylpropyl, 2-methylpropyl or 1,1-dimethylethyl, in particular methyl or ethyl.

$R^4$ is hydrogen, alkyl as stated for $R^3$ and n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl and 1-ethyl-2-methylpropyl, in particular methyl, ethyl, propyl and isopropyl, where these alkyl groups may be substituted by one or two $C_1$–$C_4$-alkoxy groups, for example alkoxyalkyl groups such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl; alkenyl, such as 2-propenyl, 2-butenyl, 3-butenyl, 1-methyl-2-propenyl, 2-methyl-2-propenyl, 2-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,2-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, or a corresponding alkenyloxy group, alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3butynyl, 1-ethyl-2-butynyl, 1-ethyl-3-butynyl, 2-ethyl-3-butynyl or 1-ethyl-1-methyl- 2-propynyl, or a corresponding alkynyloxy group, or benzyl.

Examples of very active compounds I are listed in Table A and Table B below.

TABLE A

| $R^1$ | $R^2$ | $R^3$ | $R^4$ |
|---|---|---|---|
| H | Cl | H | H |
| F | Cl | H | H |
| H | Br | H | H |
| F | Br | H | H |
| H | Cl | Cl | H |
| F | Cl | Cl | H |
| H | Br | Cl | H |
| F | Br | Cl | H |
| H | Cl | Br | H |
| F | Cl | Br | H |
| H | Br | Br | H |
| F | Br | Br | H |
| H | Cl | $CH_3$ | H |
| F | Cl | $CH_3$ | H |
| H | Br | $CH_3$ | H |
| F | Br | $CH_3$ | H |
| H | Cl | $CH_2CH_3$ | H |
| F | Cl | $CH_2CH_3$ | H |
| H | Br | $CH_2CH_3$ | H |
| F | Br | $CH_2CH_3$ | H |
| H | Cl | H | $CH_3$ |
| F | Cl | H | $CH_3$ |
| H | Br | H | $CH_3$ |
| F | Br | H | $CH_3$ |
| H | Cl | Cl | $CH_3$ |
| F | Cl | Cl | $CH_3$ |
| H | Br | Cl | $CH_3$ |
| F | Br | Cl | $CH_3$ |
| H | Cl | Br | $CH_3$ |
| F | Cl | Br | $CH_3$ |
| H | Br | Br | $CH_3$ |
| F | Br | Br | $CH_3$ |
| H | Cl | $CH_3$ | $CH_3$ |
| F | Cl | $CH_3$ | $CH_3$ |
| H | Br | $CH_3$ | $CH_3$ |
| F | Br | $CH_3$ | $CH_3$ |
| H | Cl | $CH_2CH_3$ | $CH_3$ |
| F | Cl | $CH_2CH_3$ | $CH_3$ |
| H | Br | $CH_2CH_3$ | $CH_3$ |
| F | Br | $CH_2CH_3$ | $CH_3$ |
| H | Cl | H | $CH_2CH_3$ |
| F | Cl | H | $CH_2CH_3$ |
| H | Br | H | $CH_2CH_3$ |
| F | Br | H | $CH_2CH_3$ |
| H | Cl | Cl | $CH_2CH_3$ |
| F | Cl | Cl | $CH_2CH_3$ |
| H | Br | Cl | $CH_2CH_3$ |
| F | Br | Cl | $CH_2CH_3$ |
| H | Cl | Br | $CH_2CH_3$ |
| F | Cl | Br | $CH_2CH_3$ |
| H | Br | Br | $CH_2CH_3$ |
| F | Br | Br | $CH_2CH_3$ |
| H | Cl | $CH_3$ | $CH_2CH_3$ |
| F | Cl | $CH_3$ | $CH_2CH_3$ |
| H | Br | $CH_3$ | $CH_2CH_3$ |
| F | Br | $CH_3$ | $CH_2CH_3$ |
| H | Cl | $CH_2CH_3$ | $CH_2CH_3$ |
| F | Cl | $CH_2CH_3$ | $CH_2CH_3$ |
| H | Br | $CH_2CH_3$ | $CH_2CH_3$ |
| F | Br | $CH_2CH_3$ | $CH_2CH_3$ |
| H | Cl | H | $(CH_2)_2CH_3$ |
| F | Cl | H | $(CH_2)_2CH_3$ |
| H | Cl | Cl | $(CH_2)_2CH_3$ |
| F | Cl | Cl | $(CH_2)_2CH_3$ |
| H | Cl | Br | $(CH_2)_2CH_3$ |
| F | Cl | Br | $(CH_2)_2CH_3$ |
| H | Cl | $CH_3$ | $(CH_2)_2CH_3$ |
| F | Cl | $CH_3$ | $(CH_2)_2CH_3$ |
| H | Cl | $CH_2CH_3$ | $(CH_2)_2CH_3$ |
| F | Cl | $CH_2CH_3$ | $(CH_2)_2CH_3$ |
| H | Cl | H | $CH(CH_3)_2$ |
| F | Cl | H | $CH(CH_3)_2$ |
| H | Cl | Cl | $CH(CH_3)_2$ |
| F | Cl | Cl | $CH(CH_3)_2$ |
| H | Cl | Br | $CH(CH_3)_2$ |
| F | Cl | Br | $CH(CH_3)_2$ |
| H | Cl | $CH_3$ | $CH(CH_3)_2$ |
| F | Cl | $CH_3$ | $CH(CH_3)_2$ |
| H | Cl | $CH_2CH_3$ | $CH(CH_3)_2$ |
| F | Cl | $CH_2CH_3$ | $CH(CH_3)_2$ |
| H | Cl | H | $(CH_2)_3CH_3$ |
| F | Cl | H | $(CH_2)_3CH_3$ |
| H | Cl | Cl | $(CH_2)_3CH_3$ |
| F | Cl | Cl | $(CH_2)_3CH_3$ |
| H | Cl | Br | $(CH_2)_3CH_3$ |
| F | Cl | Br | $(CH_2)_3CH_3$ |
| H | Cl | $CH_3$ | $(CH_2)_3CH_3$ |
| F | Cl | $CH_3$ | $(CH_2)_3CH_3$ |
| H | Cl | $CH_2CH_3$ | $(CH_2)_3CH_3$ |
| F | Cl | $CH_2CH_3$ | $(CH_2)_3CH_3$ |
| H | Cl | H | $CH_2CH(CH_3)_2$ |
| F | Cl | H | $CH_2CH(CH_3)_2$ |
| H | Cl | Cl | $CH_2CH(CH_3)_2$ |
| F | Cl | Cl | $CH_2CH(CH_3)_2$ |
| H | Cl | Br | $CH_2CH(CH_3)_2$ |
| F | Cl | Br | $CH_2CH(CH_3)_2$ |
| H | Cl | $CH_3$ | $CH_2CH(CH_3)_2$ |
| F | Cl | $CH_3$ | $CH_2CH(CH_3)_2$ |
| H | Cl | $CH_2CH_3$ | $CH_2CH(CH_3)_2$ |
| F | Cl | $CH_2CH_3$ | $CH_2CH(CH_3)_2$ |
| H | Cl | H | $(CH_2)_4CH_3$ |
| F | Cl | H | $(CH_2)_4CH_3$ |
| H | Cl | Cl | $(CH_2)_4CH_3$ |
| F | Cl | Cl | $(CH_2)_4CH_3$ |
| H | Cl | Br | $(CH_2)_4CH_3$ |
| F | Cl | Br | $(CH_2)_4CH_3$ |
| H | Cl | $CH_3$ | $(CH_2)_4CH_3$ |
| F | Cl | $CH_3$ | $(CH_2)_4CH_3$ |
| H | Cl | $CH_2CH_3$ | $(CH_2)_4CH_3$ |
| F | Cl | $CH_2CH_3$ | $(CH_2)_4CH_3$ |
| H | Cl | H | $(CH_2)_2CH(CH_3)_2$ |

TABLE A-continued

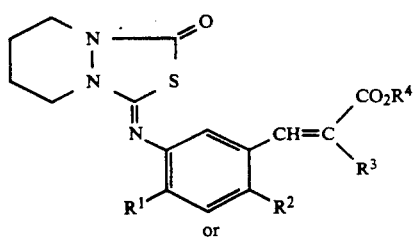

or

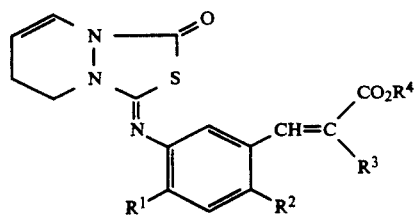

| R¹ | R² | R³ | R⁴ |
|---|---|---|---|
| F | Cl | H | (CH₂)₂CH(CH₃)₂ |
| H | Cl | Cl | (CH₂)₂CH(CH₃)₂ |
| F | Cl | Cl | (CH₂)₂CH(CH₃)₂ |
| H | Cl | Br | (CH₂)₂CH(CH₃)₂ |
| F | Cl | Br | (CH₂)₂CH(CH₃)₂ |
| H | Cl | CH₃ | (CH₂)₂CH(CH₃)₂ |
| F | Cl | CH₃ | (CH₂)₂CH(CH₃)₂ |
| H | Cl | CH₂CH₃ | (CH₂)₂CH(CH₃)₂ |
| F | Cl | CH₂CH₃ | (CH₂)₂CH(CH₃)₂ |
| H | Cl | H | (CH₂)₂OCH₃ |
| F | Cl | H | (CH₂)₂OCH₃ |
| H | Cl | Cl | (CH₂)₂OCH₃ |
| F | Cl | Cl | (CH₂)₂OCH₃ |
| H | Cl | Br | (CH₂)₂OCH₃ |
| F | Cl | Br | (CH₂)₂OCH₃ |
| H | Cl | CH₃ | (CH₂)₂OCH₃ |
| F | Cl | CH₃ | (CH₂)₂OCH₃ |
| H | Cl | CH₂CH₃ | (CH₂)₂OCH₃ |
| F | Cl | CH₂CH₃ | (CH₂)₂OCH₃ |
| H | Cl | H | CH(CH₃)CH₂OCH₃ |
| F | Cl | H | CH(CH₃)CH₂OCH₃ |
| H | Cl | Cl | CH(CH₃)CH₂OCH₃ |
| F | Cl | Cl | CH(CH₃)CH₂OCH₃ |
| H | Cl | Br | CH(CH₃)CH₂OCH₃ |
| F | Cl | Br | CH(CH₃)CH₂OCH₃ |
| H | Cl | CH₃ | CH(CH₃)CH₂OCH₃ |
| F | Cl | CH₃ | CH(CH₃)CH₂OCH₃ |
| H | Cl | CH₂CH₃ | CH(CH₃)CH₂OCH₃ |
| F | Cl | CH₂CH₃ | CH(CH₃)CH₂OCH₃ |
| H | Cl | H | CH₂CH=CH₂ |
| F | Cl | H | CH₂CH=CH₂ |
| H | Cl | Cl | CH₂CH=CH₂ |
| F | Cl | Cl | CH₂CH=CH₂ |
| H | Cl | Br | CH₂CH=CH₂ |
| F | Cl | Br | CH₂CH=CH₂ |
| H | Cl | CH₃ | CH₂CH=CH₂ |
| F | Cl | CH₃ | CH₂CH=CH₂ |
| H | Cl | CH₂CH₃ | CH₂CH=CH₂ |
| F | Cl | CH₂CH₃ | CH₂CH=CH₂ |
| H | Cl | H | CH₂CH=CHCH₃ |
| F | Cl | H | CH₂CH=CHCH₃ |
| H | Cl | Cl | CH₂CH=CHCH₃ |
| F | Cl | Cl | CH₂CH=CHCH₃ |
| H | Cl | Br | CH₂CH=CHCH₃ |
| F | Cl | Br | CH₂CH=CHCH₃ |
| H | Cl | CH₃ | CH₂CH=CHCH₃ |
| F | Cl | CH₃ | CH₂CH=CHCH₃ |
| H | Cl | CH₂CH₃ | CH₂CH=CHCH₃ |
| F | Cl | CH₂CH₃ | CH₂CH=CHCH₃ |
| H | Cl | H | CH₂C≡CH |
| F | Cl | H | CH₂C≡CH |
| H | Cl | Cl | CH₂C≡CH |
| F | Cl | Cl | CH₂C≡CH |
| H | Cl | Br | CH₂C≡CH |
| F | Cl | Br | CH₂C≡CH |
| H | Cl | CH₃ | CH₂C≡CH |
| F | Cl | CH₃ | CH₂C≡CH |
| H | Cl | CH₂CH₃ | CH₂C≡CH |

TABLE A-continued

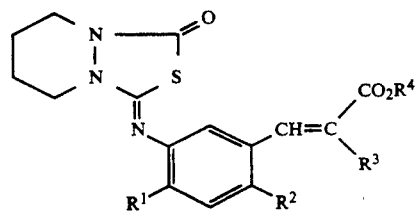

or

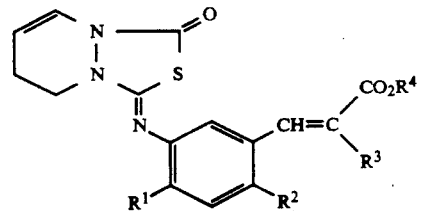

| R¹ | R² | R³ | R⁴ |
|---|---|---|---|
| F | Cl | CH₂CH₃ | CH₂C≡CH |
| H | Cl | H | CH₂C≡CCH₃ |
| F | Cl | H | CH₂C≡CCH₃ |
| H | Cl | Cl | CH₂C≡CCH₃ |
| F | Cl | Cl | CH₂C≡CCH₃ |
| H | Cl | Br | CH₂C≡CCH₃ |
| F | Cl | Br | CH₂C≡CCH₃ |
| H | Cl | CH₃ | CH₂C≡CCH₃ |
| F | Cl | CH₃ | CH₂C≡CCH₃ |
| H | Cl | CH₂CH₃ | CH₂C≡CCH₃ |
| F | Cl | CH₂CH₃ | CH₂C≡CCH₃ |
| H | Cl | H | CH₂Ph |
| F | Cl | H | CH₂Ph |
| H | Cl | Cl | CH₂Ph |
| F | Cl | Cl | CH₂Ph |
| H | Cl | Br | CH₂Ph |
| F | Cl | Br | CH₂Ph |
| H | Cl | CH₃ | CH₂Ph |
| F | Cl | CH₃ | CH₂Ph |
| H | Cl | CH₂CH₃ | CH₂Ph |
| F | Cl | CH₂CH₃ | CH₂Ph |
| H | F | Cl | CH₃ |
| H | F | Br | CH₃ |
| H | F | CH₃ | CH₃ |
| H | F | Cl | CH₂CH₃ |
| H | F | Br | CH₂CH₃ |
| H | F | CH₃ | CH₂CH₃ |
| H | F | Cl | (CH₂)₂CH₃ |
| H | F | Br | (CH₂)₂CH₃ |
| H | F | CH₃ | (CH₂)₂CH₃ |
| H | F | Cl | CH(CH₃)₂ |
| H | F | Br | CH(CH₃)₂ |
| H | F | CH₃ | CH(CH₃)₂ |
| H | F | Cl | (CH₂)₃CH₃ |
| H | F | Br | (CH₂)₃CH₃ |
| H | F | CH₃ | (CH₂)₃CH₃ |
| H | F | Cl | CH₂CH(CH₃)₂ |
| H | F | Br | CH₂CH(CH₃)₂ |
| H | F | CH₃ | CH₂CH(CH₃)₂ |
| H | F | Cl | (CH₂)₄CH₃ |
| H | F | Br | (CH₂)₄CH₃ |
| H | F | CH₃ | (CH₂)₄CH₃ |
| H | F | Cl | (CH₂)₂CH(CH₃)₂ |
| H | F | Br | (CH₂)₂CH(CH₃)₂ |
| H | F | CH₃ | (CH₂)₂CH(CH₃)₂ |
| H | F | Cl | (CH₂)₂OCH₃ |
| H | F | Br | (CH₂)₂OCH₃ |
| H | F | CH₃ | (CH₂)₂OCH₃ |
| H | F | Cl | CH(CH₃)CH₂OCH₃ |
| H | F | Br | CH(CH₃)CH₂OCH₃ |
| H | F | CH₃ | CH(CH₃)CH₂OCH₃ |
| H | F | Cl | CH₂CH=CH₂ |
| H | F | Br | CH₂CH=CH₂ |
| H | F | CH₃ | CH₂CH=CH₂ |
| H | F | Cl | CH₂CH=CHCH₃ |
| H | F | Br | CH₂CH=CHCH₃ |
| H | F | CH₃ | CH₂CH=CHCH₃ |
| H | F | Cl | CH₂C≡CH |

TABLE A-continued

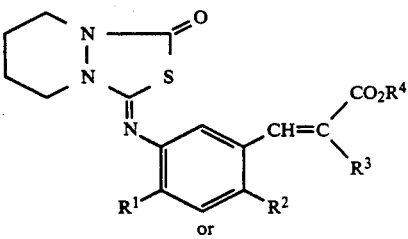

or

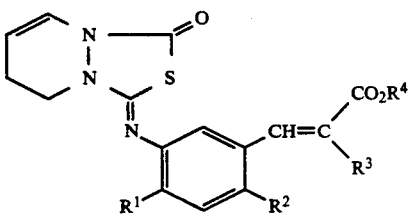

| R[1] | R[2] | R[3] | R[4] |
|---|---|---|---|
| H | F | Br | CH$_2$C≡CH |
| H | F | CH$_3$ | CH$_2$C≡CH |
| H | F | Cl | CH$_2$C≡CCH$_3$ |
| H | F | Br | CH$_2$C≡CCH$_3$ |
| H | F | CH$_3$ | CH$_2$C≡CCH$_3$ |
| H | F | Cl | CH$_2$Ph |
| H | F | Br | CH$_2$Ph |
| H | F | CH$_3$ | CH$_2$Ph |

TABLE B

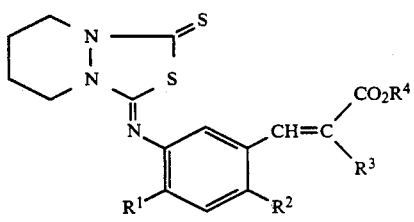

or

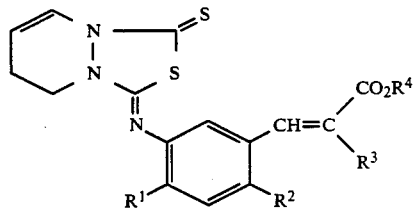

| R[1] | R[2] | R[3] | R[4] |
|---|---|---|---|
| H | Cl | H | H |
| F | Cl | H | H |
| H | Br | H | H |
| F | Br | H | H |
| H | Cl | Cl | H |
| F | Cl | Cl | H |
| H | Br | Cl | H |
| F | Br | Cl | H |
| H | Cl | Br | H |
| F | Cl | Br | H |
| H | Br | Br | H |
| F | Br | Br | H |
| H | Cl | CH$_3$ | H |
| F | Cl | CH$_3$ | H |
| H | Br | CH$_3$ | H |
| F | Br | CH$_3$ | H |
| H | Cl | CH$_2$CH$_3$ | H |
| F | Cl | CH$_2$CH$_3$ | H |
| H | Br | CH$_2$CH$_3$ | H |
| F | Br | CH$_2$CH$_3$ | H |
| H | Cl | H | CH$_3$ |
| F | Cl | H | CH$_3$ |

TABLE B-continued

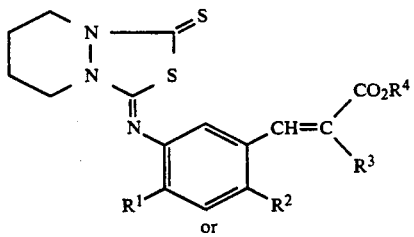

or

| R[1] | R[2] | R[3] | R[4] |
|---|---|---|---|
| H | Br | H | CH$_3$ |
| F | Br | H | CH$_3$ |
| H | Cl | Cl | CH$_3$ |
| F | Cl | Cl | CH$_3$ |
| H | Br | Cl | CH$_3$ |
| F | Br | Cl | CH$_3$ |
| H | Cl | Br | CH$_3$ |
| F | Cl | Br | CH$_3$ |
| H | Br | Br | CH$_3$ |
| F | Br | Br | CH$_3$ |
| H | Cl | CH$_3$ | CH$_3$ |
| F | Cl | CH$_3$ | CH$_3$ |
| H | Br | CH$_3$ | CH$_3$ |
| F | Br | CH$_3$ | CH$_3$ |
| H | Cl | CH$_2$CH$_3$ | CH$_3$ |
| F | Cl | CH$_2$CH$_3$ | CH$_3$ |
| H | Br | CH$_2$CH$_3$ | CH$_3$ |
| F | Br | CH$_2$CH$_3$ | CH$_3$ |
| H | Cl | H | CH$_2$CH$_3$ |
| F | Cl | H | CH$_2$CH$_3$ |
| H | Br | H | CH$_2$CH$_3$ |
| F | Br | H | CH$_2$CH$_3$ |
| H | Cl | Cl | CH$_2$CH$_3$ |
| F | Cl | Cl | CH$_2$CH$_3$ |
| H | Br | Cl | CH$_2$CH$_3$ |
| F | Br | Cl | CH$_2$CH$_3$ |
| H | Cl | Br | CH$_2$CH$_3$ |
| F | Cl | Br | CH$_2$CH$_3$ |
| H | Br | Br | CH$_2$CH$_3$ |
| F | Br | Br | CH$_2$CH$_3$ |
| H | Cl | CH$_3$ | CH$_2$CH$_3$ |
| F | Cl | CH$_3$ | CH$_2$CH$_3$ |
| H | Br | CH$_3$ | CH$_2$CH$_3$ |
| F | Br | CH$_3$ | CH$_2$CH$_3$ |
| H | Cl | CH$_2$CH$_3$ | CH$_2$CH$_3$ |
| F | Cl | CH$_2$CH$_3$ | CH$_2$CH$_3$ |
| H | Br | CH$_2$CH$_3$ | CH$_2$CH$_3$ |
| F | Br | CH$_2$CH$_3$ | CH$_2$CH$_3$ |
| H | Cl | H | (CH$_2$)$_2$CH$_3$ |
| F | Cl | H | (CH$_2$)$_2$CH$_3$ |
| H | Cl | Cl | (CH$_2$)$_2$CH$_3$ |
| F | Cl | Cl | (CH$_2$)$_2$CH$_3$ |
| H | Cl | Br | (CH$_2$)$_2$CH$_3$ |
| F | Cl | Br | (CH$_2$)$_2$CH$_3$ |
| H | Cl | CH$_3$ | (CH$_2$)$_2$CH$_3$ |
| F | Cl | CH$_3$ | (CH$_2$)$_2$CH$_3$ |
| H | Cl | CH$_2$CH$_3$ | (CH$_2$)$_2$CH$_3$ |
| F | Cl | CH$_2$CH$_3$ | (CH$_2$)$_2$CH$_3$ |
| H | Cl | H | CH(CH$_3$)$_2$ |
| F | Cl | H | CH(CH$_3$)$_2$ |
| H | Cl | Cl | CH(CH$_3$)$_2$ |
| F | Cl | Cl | CH(CH$_3$)$_2$ |
| H | Cl | Br | CH(CH$_3$)$_2$ |
| F | Cl | Br | CH(CH$_3$)$_2$ |
| H | Cl | CH$_3$ | CH(CH$_3$)$_2$ |
| F | Cl | CH$_3$ | CH(CH$_3$)$_2$ |
| H | Cl | CH$_2$CH$_3$ | CH(CH$_3$)$_2$ |
| F | Cl | CH$_2$CH$_3$ | CH(CH$_3$)$_2$ |

TABLE B-continued

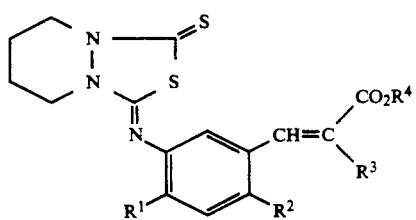

or

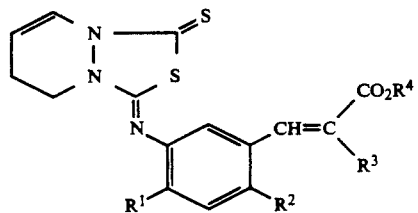

| R¹ | R² | R³ | R⁴ |
|---|---|---|---|
| H | Cl | H | (CH₂)₃CH₃ |
| F | Cl | H | (CH₂)₃CH₃ |
| H | Cl | Cl | (CH₂)₃CH₃ |
| F | Cl | Cl | (CH₂)₃CH₃ |
| H | Cl | Br | (CH₂)₃CH₃ |
| F | Cl | Br | (CH₂)₃CH₃ |
| H | Cl | CH₃ | (CH₂)₃CH₃ |
| F | Cl | CH₃ | (CH₂)₃CH₃ |
| H | Cl | CH₂CH₃ | (CH₂)₃CH₃ |
| F | Cl | CH₂CH₃ | (CH₂)₃CH₃ |
| H | Cl | H | CH₂CH(CH₃)₂ |
| F | Cl | H | CH₂CH(CH₃)₂ |
| H | Cl | Cl | CH₂CH(CH₃)₂ |
| F | Cl | Cl | CH₂CH(CH₃)₂ |
| H | Cl | Br | CH₂CH(CH₃)₂ |
| F | Cl | Br | CH₂CH(CH₃)₂ |
| H | Cl | CH₃ | CH₂CH(CH₃)₂ |
| F | Cl | CH₃ | CH₂CH(CH₃)₂ |
| H | Cl | CH₂CH₃ | CH₂CH(CH₃)₂ |
| F | Cl | CH₂CH₃ | CH₂CH(CH₃)₂ |
| H | Cl | H | (CH₂)₄CH₃ |
| F | Cl | H | (CH₂)₄CH₃ |
| H | Cl | Cl | (CH₂)₄CH₃ |
| F | Cl | Cl | (CH₂)₄CH₃ |
| H | Cl | Br | (CH₂)₄CH₃ |
| F | Cl | Br | (CH₂)₄CH₃ |
| H | Cl | CH₃ | (CH₂)₄CH₃ |
| F | Cl | CH₃ | (CH₂)₄CH₃ |
| H | Cl | CH₂CH₃ | (CH₂)₄CH₃ |
| F | Cl | CH₂CH₃ | (CH₂)₄CH₃ |
| H | Cl | H | (CH₂)₂CH(CH₃)₂ |
| F | Cl | H | (CH₂)₂CH(CH₃)₂ |
| H | Cl | Cl | (CH₂)₂CH(CH₃)₂ |
| F | Cl | Cl | (CH₂)₂CH(CH₃)₂ |
| H | Cl | Br | (CH₂)₂CH(CH₃)₂ |
| F | Cl | Br | (CH₂)₂CH(CH₃)₂ |
| H | Cl | CH₃ | (CH₂)₂CH(CH₃)₂ |
| F | Cl | CH₃ | (CH₂)₂CH(CH₃)₂ |
| H | Cl | CH₂CH₃ | (CH₂)₂CH(CH₃)₂ |
| F | Cl | CH₂CH₃ | (CH₂)₂CH(CH₃)₂ |
| H | Cl | H | (CH₂)₂OCH₃ |
| F | Cl | H | (CH₂)₂OCH₃ |
| H | Cl | Cl | (CH₂)₂OCH₃ |
| F | Cl | Cl | (CH₂)₂OCH₃ |
| H | Cl | Br | (CH₂)₂OCH₃ |
| F | Cl | Br | (CH₂)₂OCH₃ |
| H | Cl | CH₃ | (CH₂)₂OCH₃ |
| F | Cl | CH₃ | (CH₂)₂OCH₃ |
| H | Cl | CH₂CH₃ | (CH₂)₂OCH₃ |
| F | Cl | CH₂CH₃ | (CH₂)₂OCH₃ |
| H | Cl | H | CH(CH₃)CH₂OCH₃ |
| F | Cl | H | CH(CH₃)CH₂OCH₃ |
| H | Cl | Cl | CH(CH₃)CH₂OCH₃ |
| F | Cl | Cl | CH(CH₃)CH₂OCH₃ |
| H | Cl | Br | CH(CH₃)CH₂OCH₃ |
| F | Cl | Br | CH(CH₃)CH₂OCH₃ |
| H | Cl | CH₃ | CH(CH₃)CH₂OCH₃ |
| F | Cl | CH₃ | CH(CH₃)CH₂OCH₃ |

TABLE B-continued

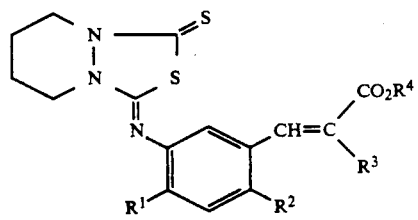

or

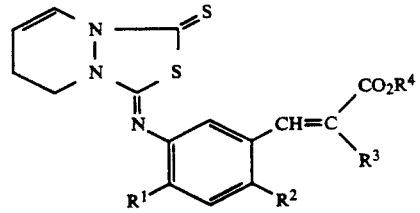

| R¹ | R² | R³ | R⁴ |
|---|---|---|---|
| H | Cl | CH₂CH₃ | CH(CH₃)CH₂OCH₃ |
| F | Cl | CH₂CH₃ | CH(CH₃)CH₂OCH₃ |
| H | Cl | H | CH₂CH=CH₂ |
| F | Cl | H | CH₂CH=CH₂ |
| H | Cl | Cl | CH₂CH=CH₂ |
| F | Cl | Cl | CH₂CH=CH₂ |
| H | Cl | Br | CH₂CH=CH₂ |
| F | Cl | Br | CH₂CH=CH₂ |
| H | Cl | CH₃ | CH₂CH=CH₂ |
| F | Cl | CH₃ | CH₂CH=CH₂ |
| H | Cl | CH₂CH₃ | CH₂CH=CH₂ |
| F | Cl | CH₂CH₃ | CH₂CH=CH₂ |
| H | Cl | H | CH₂CH=CHCH₃ |
| F | Cl | H | CH₂CH=CHCH₃ |
| H | Cl | Cl | CH₂CH=CHCH₃ |
| F | Cl | Cl | CH₂CH=CHCH₃ |
| H | Cl | Br | CH₂CH=CHCH₃ |
| F | Cl | Br | CH₂CH=CHCH₃ |
| H | Cl | CH₃ | CH₂CH=CHCH₃ |
| F | Cl | CH₃ | CH₂CH=CHCH₃ |
| H | Cl | CH₂CH₃ | CH₂CH=CHCH₃ |
| F | Cl | CH₂CH₃ | CH₂CH=CHCH₃ |
| H | Cl | H | CH₂C≡CH |
| F | Cl | H | CH₂C≡CH |
| H | Cl | Cl | CH₂C≡CH |
| F | Cl | Cl | CH₂C≡CH |
| H | Cl | Br | CH₂C≡CH |
| F | Cl | Br | CH₂C≡CH |
| H | Cl | CH₃ | CH₂C≡CH |
| F | Cl | CH₃ | CH₂C≡CH |
| H | Cl | CH₂CH₃ | CH₂C≡CH |
| F | Cl | CH₂CH₃ | CH₂C≡CH |
| H | Cl | H | CH₂C≡CCH₃ |
| F | Cl | H | CH₂C≡CCH₃ |
| H | Cl | Cl | CH₂C≡CCH₃ |
| F | Cl | Cl | CH₂C≡CCH₃ |
| H | Cl | Br | CH₂C≡CCH₃ |
| F | Cl | Br | CH₂C≡CCH₃ |
| H | Cl | CH₃ | CH₂C≡CCH₃ |
| F | Cl | CH₃ | CH₂C≡CCH₃ |
| H | Cl | CH₂CH₃ | CH₂C≡CCH₃ |
| F | Cl | CH₂CH₃ | CH₂C≡CCH₃ |
| H | Cl | H | CH₂Ph |
| F | Cl | H | CH₂Ph |
| H | Cl | Cl | CH₂Ph |
| F | Cl | Cl | CH₂Ph |
| H | Cl | Br | CH₂Ph |
| F | Cl | Br | CH₂Ph |
| H | Cl | CH₃ | CH₂Ph |
| F | Cl | CH₃ | CH₂Ph |
| H | Cl | CH₂CH₃ | CH₂Ph |
| F | Cl | CH₂CH₃ | CH₂Ph |
| H | F | H | CH₃ |
| H | F | Br | CH₃ |
| H | F | CH₃ | CH₃ |
| H | F | Cl | CH₂CH₃ |
| H | F | Br | CH₂CH₃ |
| H | F | CH₃ | CH₂CH₃ |

TABLE B-continued

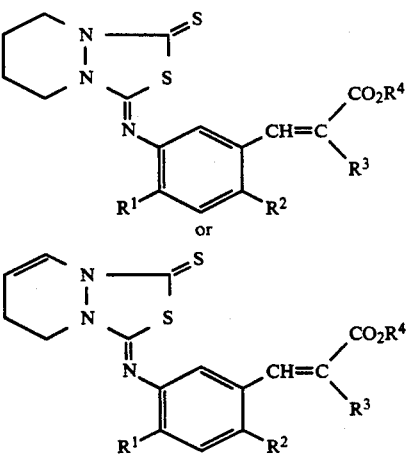

| R¹ | R² | R³ | R⁴ |
|---|---|---|---|
| H | F | Cl | (CH₂)₂CH₃ |
| H | F | Br | (CH₂)₂CH₃ |
| H | F | CH₃ | (CH₂)₂CH₃ |
| H | F | Cl | CH(CH₃)₂ |
| H | F | Br | CH(CH₃)₂ |
| H | F | CH₃ | CH(CH₃)₂ |
| H | F | Cl | (CH₂)₃CH₃ |
| H | F | Br | (CH₂)₃CH₃ |
| H | F | CH₃ | (CH₂)₃CH₃ |
| H | F | Cl | CH₂CH(CH₃)₂ |
| H | F | Br | CH₂CH(CH₃)₂ |
| H | F | CH₃ | CH₂CH(CH₃)₂ |
| H | F | Cl | (CH₂)₄CH₃ |
| H | F | Br | (CH₂)₄CH₃ |
| H | F | CH₃ | (CH₂)₄CH₃ |
| H | F | Cl | (CH₂)₂CH(CH₃)₂ |
| H | F | Br | (CH₂)₂CH(CH₃)₂ |
| H | F | CH₃ | (CH₂)₂CH(CH₃)₂ |
| H | F | Cl | (CH₂)₂OCH₃ |
| H | F | Br | (CH₂)₂OCH₃ |
| H | F | CH₃ | (CH₂)₂OCH₃ |
| H | F | Cl | CH(CH₃)CH₂OCH₃ |
| H | F | Br | CH(CH₃)CH₂OCH₃ |
| H | F | CH₃ | CH(CH₃)CH₂OCH₃ |
| H | F | Cl | CH₂CH=CH₂ |
| H | F | Br | CH₂CH=CH₂ |
| H | F | CH₃ | CH₂CH=CH₂ |
| H | F | Cl | CH₂CH=CHCH₃ |
| H | F | Br | CH₂CH=CHCH₃ |
| H | F | CH₃ | CH₂CH=CHCH₃ |
| H | F | Cl | CH₂C≡CH |
| H | F | Br | CH₂C≡CH |
| H | F | CH₃ | CH₂C≡CH |
| H | F | Cl | CH₂C≡CCH₃ |
| H | F | Br | CH₂C≡CCH₃ |
| H | F | CH₃ | CH₂C≡CCH₃ |
| H | F | Cl | CH₂Ph |
| H | F | Br | CH₂Ph |
| H | F | CH₃ | CH₂Ph |

The cinnamic esters I, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of 90 to 100% (according to the NMR spectrum).

Examples of formulations are as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.001 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.001 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.001 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.001 is intimately mixed with 97 parts by weight of particulate kaolin. A dust is obtained containing 3% by weight of the active ingredient.

VII. 30 parts by weight of compound no. 1.001 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.001 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the numerous application methods possible, the compounds according to the invention, or agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |

| Botanical name | Common name |
|---|---|
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the cinnamic esters I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acid derivatives (salts, esters, amides), etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

Example 1

9-[E/Z-(3-{2-methoxycarbonyl-prop-1-enyl}-4-chlorophenylamino)]-8-thia-1,6-diazabicyclo[4.3.0]-nonan-7-one

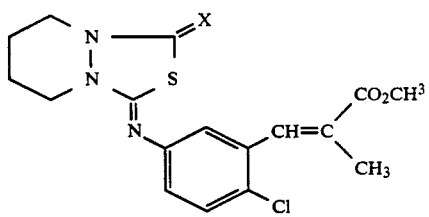

a) At 5° C., 167.4 g (1.8 mol) of α-picoline was added to 468 g (1.8 mol) of 2-chloro-5-nitro-α-methylcinnamyl chloride in 2250 ml of methanol. The reaction mixture was stirred for 12 hours at 23° C. Cooling to 0° C. yielded the solid product.

Yield: 294 g (64%) of methyl 2-chloro-5-nitro-α-methylcinnamate; mp. 95°–96° C.

b) At 70° C., a mixture of 250 ml of methanol, 350 ml of glacial acetic acid and 105 g of nitrocinnamate (0.4 mol) was added to a mixture of 149 g of iron powder and 120 ml of glacial acetic acid. After 90 minutes at the boiling temperature, the reaction mixture was separated from solids, and the solution obtained was taken up in water and extracted. 81.1 g (88%) of methyl 2-chloro-5-amino-α-methylcinnamate (mp. 80° C.) was obtained from the organic phase.

c) At 25°–30° C., 11.3 g (0.05 mol) of the product from b) in 100 ml of methanol was added to a mixture of 6.3 g (0.055 mol) of thiophosgene, 50 ml of methylene chloride and 100 ml of water. Upon completion of the reaction (TLC) the organic phase was separated. There was obtained from it 12.5 g (93%) of methyl 2-chloro-5-isothiocyanato-α-methylcinnamate (mp. 60°–61° C.).

d) At 25°–30° C., 12.0 g (0.045 mol) of the product from c) in 50 ml of tetrahydrofuran was added to a mixture of 4.3 g (0.05 mol) of piperidazine in 200 ml of tetrahydrofuran. Upon completion of the reaction (TLC) the solvent was removed and the residue thus obtained was washed and dried. There was obtained 12.0 g (75%) of N-(4-chloro-3-[-2-methoxycarbonyl-prop-1-enyl]-phenylthiocarbamoyl)-hexahydropyridazine (mp. 120°–121° C.).

e) At 25°–30° C., 2.2 g (0.011 mol) of trimethyl chloroformate in 20 ml of methylene chloride was added to a mixture of 3.5 g (0.01 mol) of the product from d) and 1.7 g (0.02 mol) of pyridine in 130 ml of methylene chloride. After the mixture had been kept for 2 hours at 25° C., it was washed neutral and evaporated down. 2.0 g (53%) of the title compound was obtained after chromatographic purification (Table 1, no. 1.001).

The directions given in the synthesis example above were employed, after appropriate modification of the starting compounds, for manufacturing further compounds I.

TABLE 1

| Compound No. | R¹ | R² | R³ | R⁴ | X | Phys. data [(mp.(°C.); IR(cm⁻¹)] |
|---|---|---|---|---|---|---|
| 1.001 | H | Cl | CH₃ | CH₃ | O | 123–124 |
| 1.002 | H | Cl | Br | CH₃ | O | 1728, 1713, 1624, 1247, 1221 |
| 1.003 | H | Cl | Cl | C₂H₅ | O | 1717, 1619, 1248, 1221 |

TABLE 2

| Compound No. | R¹ | R² | R³ | R⁴ | X | Phys. data [(mp.(°C.); IR(cm⁻¹)] |
|---|---|---|---|---|---|---|
| 2.001 | H | Cl | Cl | CH₃ | O | 109–111 |
| 2.002 | H | Cl | Br | CH₃ | O | 105–107 |
| 2.003 | H | Cl | Br | C(CH₃)₃ | O | 1706, 1625, 1270, 1154 |
| 2.004 | H | Cl | Cl | C(CH₃)₃ | O | 1709, 1627, 1273, 1158 |
| 2.005 | H | Cl | Br | CH(CH₃)₂ | O | 120–121 |
| 2.006 | H | Cl | Cl | CH(CH₃)₂ | O | 134–135 |

TABLE 2-continued

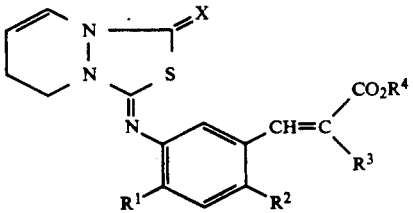

| Compound No. | $R^1$ | $R^2$ | $R^3$ | $R^4$ | X | Phys. data [(mp.(°C.); IR(cm$^{-1}$)] |
|---|---|---|---|---|---|---|
| 2.007 | H | Cl | Br | $C_2H_5$ | O | 125-126 |
| 2.008 | H | Cl | Cl | $C_2H_5$ | O | 105-106 |
| 2.009 | H | Cl | Cl | $C_2H_5$ | S | 100-102 |
| 2.010 | H | Cl | Cl | $CH(CH_3)_2$ | S | 143-145 |
| 2.011 | H | Cl | Br | $CH_3$ | S | 102-103 |
| 2.012 | H | Cl | Br | $CH(CH_3)_2$ | S | 142-143 |

USE EXAMPLES

The herbicidal action of the cinnamic esters of the formula I is illustrated in the following greenhouse experiments.

The vessels employed were plastic flowerpots having a volume of 300 cm$^3$ and filled with a sandy loam containing about 3.0% humus. The seeds of the test plants were sown separately, according to species.

For the preemergence treatment, the active ingredients were suspended or emulsified in water and sprayed through finely distributing nozzles immediately after sowing. The vessels were lightly irrigated to induce germination and growth, and then covered with plastic hoods until the plants had emerged. This cover ensured uniform germination of the plants, insofar as this was not impaired by the active ingredients.

For the postemergence treatment, the plants were grown, depending on growth form, to a height of 3 to 15 cm before being treated with the active ingredients, which were suspended or emulsified in water. The application rate for postemergence treatment was 0.06 kg/ha.

The plants were kept according to their specific requirements, at temperatures of 10°-25° C., or 20°-35° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were *Chenopodium album*, *Galium aparine*, and *Triticum aestivum*.

Compound 1.001, applied postemergence at a rate of 0.06 kg/ha, combated unwanted broadleaved plants very well and was at the same time tolerated by the crop plant.

We claim:

1. Cinnamic esters of the formula I

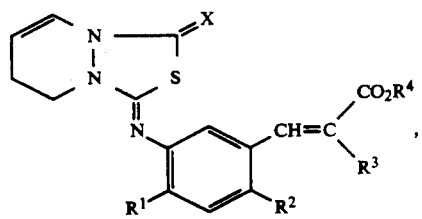

where $R^1$ is hydrogen or fluorine, $R^2$ is halogen, $R^3$ is hydrogen, halogen or $C_1$-$C_4$-alkyl, $R^4$ is hydrogen, $C_1$-$C_6$-alkyl which may be substituted by one or two $C_1$-$C_4$-alkoxy groups, or is $C_3$-$C_6$-alkenyl, $C_3$-$C_6$-alkynyl or benzyl, and X is oxygen or sulfur.

2. Cinnamic esters of the formula I

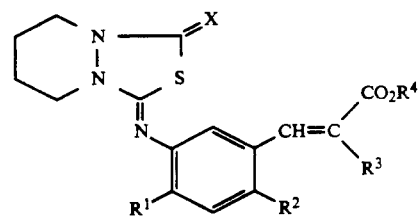

wherein $R^1$ is hydrogen or fluorine, $R^2$ is halogen, $R^3$ is halogen, $R^4$ is hydrogen, $C_1$-$C_6$-alkyl which may be substituted by one or two $C_1$-$C_4$-alkoxy groups, or is $C_3$-$C_6$-alkenyl, $C_3$-$C_6$-alkynyl or benzyl, and X is oxygen or sulfur.

3. A herbicidal composition which comprises a herbicidally effective amount of a cinnamic ester of the formula I as set forth in claim 1 and conventional inert additives.

4. A herbicidal composition which comprises a herbicidally effective amount of a cinnamic ester of the formula I as set forth in claim 2 and conventional inert additives.

5. A process for combating the growth of unwanted plants, wherein the unwanted plants and/or their habitat are treated with a herbicidally effective amount of a cinnamic ester I as set forth in claim 1.

6. A process for combating the growth of unwanted plants, wherein the unwanted plants and/or their habitat are treated with a herbicidally effective amount of a cinnamic ester I as set forth in claim 2.

* * * * *

UNITED STATES PATENT AND TRADEMARK OFFICE
CERTIFICATE OF CORRECTION

PATENT NO. : 5,296,451
DATED : March 22, 1994
INVENTOR(S) : RUEB et al.

It is certified that error appears in the above-indentified patent and that said Letters Patent is hereby corrected as shown below:

On the cover page, under Item [30], the priority date should be --July 26, 1989--.

Signed and Sealed this

Sixteenth Day of August, 1994

Attest:

BRUCE LEHMAN

Attesting Officer     Commissioner of Patents and Trademarks